(12) United States Patent
Trollsas et al.

(10) Patent No.: US 8,685,430 B1
(45) Date of Patent: *Apr. 1, 2014

(54) TAILORED ALIPHATIC POLYESTERS FOR STENT COATINGS

(75) Inventors: Mikael Trollsas, San Jose, CA (US); Lothar W. Kleiner, Los Altos, CA (US); Syed F. A. Hossainy, Fremont, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 1168 days.

This patent is subject to a terminal disclaimer.

(21) Appl. No.: 11/827,783

(22) Filed: Jul. 13, 2007

Related U.S. Application Data

(60) Provisional application No. 60/830,823, filed on Jul. 14, 2006.

(51) Int. Cl.
*A61F 2/00* (2006.01)
*A61L 27/34* (2006.01)

(52) U.S. Cl.
CPC ........................................ A61L 27/34 (2013.01)
USPC ........................................................ 424/425

(58) Field of Classification Search
None
See application file for complete search history.

(56) References Cited

U.S. PATENT DOCUMENTS

| | | |
|---|---|---|
| 4,329,383 A | 5/1982 | Joh |
| 4,613,665 A | 9/1986 | Larm |
| 4,733,665 A | 3/1988 | Palmaz |
| 4,800,882 A | 1/1989 | Gianturco |
| 4,882,168 A | 11/1989 | Casey et al. |
| 4,886,062 A | 12/1989 | Wiktor |
| 4,916,193 A | 4/1990 | Tang et al. |
| 4,941,870 A | 7/1990 | Okada et al. |
| 4,977,901 A | 12/1990 | Ofstead |
| 4,994,071 A | 2/1991 | MacGregor |
| 5,064,817 A | 11/1991 | Yedgar et al. |
| 5,092,877 A | 3/1992 | Pinchuk |
| 5,112,457 A | 5/1992 | Marchant |
| 5,163,952 A | 11/1992 | Froix |
| 5,165,919 A | 11/1992 | Sasaki et al. |
| 5,182,317 A | 1/1993 | Winters et al. |
| 5,262,451 A | 11/1993 | Winters et al. |
| 5,272,012 A | 12/1993 | Opolski |
| 5,292,516 A | 3/1994 | Viegas et al. |
| 5,298,260 A | 3/1994 | Viegas et al. |
| 5,300,295 A | 4/1994 | Viegas et al. |
| 5,304,121 A | 4/1994 | Sahatjian |
| 5,306,501 A | 4/1994 | Viegas et al. |
| 5,328,471 A | 7/1994 | Slepian |
| 5,330,768 A | 7/1994 | Park et al. |
| 5,338,770 A | 8/1994 | Winters et al. |
| 5,380,299 A | 1/1995 | Fearnot et al. |
| 5,417,981 A | 5/1995 | Endo et al. |
| 5,447,724 A | 9/1995 | Helmus et al. |
| 5,455,040 A | 10/1995 | Marchant |
| 5,462,990 A | 10/1995 | Hubbell et al. |
| 5,464,650 A | 11/1995 | Berg et al. |
| 5,569,463 A | 10/1996 | Helmus et al. |
| 5,578,073 A | 11/1996 | Haimovich et al. |
| 5,605,696 A | 2/1997 | Eury et al. |
| 5,609,629 A | 3/1997 | Fearnot et al. |
| 5,624,411 A | 4/1997 | Tuch |
| 5,628,730 A | 5/1997 | Shapland et al. |
| 5,649,977 A | 7/1997 | Campbell |
| 5,658,995 A | 8/1997 | Kohn et al. |
| 5,667,767 A | 9/1997 | Greff et al. |
| 5,670,558 A | 9/1997 | Onishi et al. |
| 5,679,400 A | 10/1997 | Tuch |
| 5,700,286 A | 12/1997 | Tartaglia et al. |
| 5,702,754 A | 12/1997 | Zhong |
| 5,716,981 A | 2/1998 | Hunter et al. |
| 5,735,897 A | 4/1998 | Buirge |
| 5,746,998 A | 5/1998 | Torchilin et al. |
| 5,776,184 A | 7/1998 | Tuch |
| 5,788,979 A | 8/1998 | Alt et al. |
| 5,800,392 A | 9/1998 | Racchini |
| 5,820,917 A | 10/1998 | Tuch |
| 5,824,048 A | 10/1998 | Tuch |
| 5,824,049 A | 10/1998 | Ragheb et al. |
| 5,830,178 A | 11/1998 | Jones et al. |
| 5,837,008 A | 11/1998 | Berg et al. |
| 5,837,313 A | 11/1998 | Ding et al. |
| 5,851,508 A | 12/1998 | Greff et al. |
| 5,858,746 A | 1/1999 | Hubbell et al. |
| 5,865,814 A | 2/1999 | Tuch |
| 5,869,127 A | 2/1999 | Zhong |
| 5,873,904 A | 2/1999 | Ragheb et al. |
| 5,876,433 A | 3/1999 | Lunn |
| 5,877,224 A | 3/1999 | Brocchini et al. |
| 5,925,720 A | 7/1999 | Kataoka et al. |
| 5,955,509 A | 9/1999 | Webber et al. |

(Continued)

FOREIGN PATENT DOCUMENTS

| | | |
|---|---|---|
| EP | 0 301 856 | 2/1989 |
| EP | 0 514 406 | 11/1992 |

(Continued)

OTHER PUBLICATIONS

U.S. Appl. No. 09/406,473, filed Sep. 27, 1999, Pacetti.
U.S. Appl. No. 09/894,293, filed Jun. 27, 2001, Roorda et al.
U.S. Appl. No. 09/966,786, filed Sep. 27, 2001, Hossainy.
U.S. Appl. No. 09/967,632, filed Sep. 28, 2001, Pacetti.
U.S. Appl. No. 10/040,538, filed Dec. 28, 2001, Pacetti et al.
U.S. Appl. No. 10/104,772, filed Mar. 20, 2002, Dutta.
U.S. Appl. No. 10/177,154, filed Jun. 21, 2002, Hossainy et al.
U.S. Appl. No. 10/177,942, filed Jun. 21, 2002, Michal et al.
U.S. Appl. No. 10/246,883, filed Sep. 18, 2002, Taylor.
U.S. Appl. No. 10/260,182, filed Sep. 27, 2002, Hossainy.
U.S. Appl. No. 10/271,851, filed Oct. 15, 2002, Roorda.
U.S. Appl. No. 10/286,058, filed Oct. 31, 2002, Pacetti et al.
U.S. Appl. No. 10/316,739, filed Dec. 10, 2002, Zhang et al.
U.S. Appl. No. 10/327,371, filed Dec. 19, 2002, Lin et al.
U.S. Appl. No. 10/330,412, field Dec. 27, 2002, Hossainy et al.
U.S. Appl. No. 10/375,496, filed Feb. 26, 2003, Esbeck.
U.S. Appl. No. 10/376,027, filed Feb. 26, 2003, Kokish et al.
U.S. Appl. No. 10/376,348, filed Feb. 26, 2003, Ding et al.
U.S. Appl. No. 10/428,691, filed May 1, 2003, Pacetti.
U.S. Appl. No. 10/606,711, field Jun. 26, 2003, Pacetti.
U.S. Appl. No. 10/631,116, filed Jul. 31, 2003, Dehnad.

(Continued)

*Primary Examiner* — Bethany Barham
(74) *Attorney, Agent, or Firm* — Squire Sanders (US) LLP

(57) ABSTRACT

A aliphatic polyester polymer for stent coating is described.

10 Claims, 1 Drawing Sheet

(56) References Cited

U.S. PATENT DOCUMENTS

| | | |
|---|---|---|
| 5,971,954 A | 10/1999 | Conway et al. |
| 5,980,928 A | 11/1999 | Terry |
| 5,980,972 A | 11/1999 | Ding |
| 5,997,517 A | 12/1999 | Whitbourne |
| 6,001,117 A | 12/1999 | Huxel et al. |
| 6,010,530 A | 1/2000 | Goicoechea |
| 6,015,541 A | 1/2000 | Greff et al. |
| 6,033,582 A | 3/2000 | Lee et al. |
| 6,042,875 A | 3/2000 | Ding et al. |
| 6,051,576 A | 4/2000 | Ashton et al. |
| 6,051,648 A | 4/2000 | Rhee et al. |
| 6,056,993 A | 5/2000 | Leidner et al. |
| 6,060,451 A | 5/2000 | DiMaio et al. |
| 6,060,518 A | 5/2000 | Kabanov et al. |
| 6,080,488 A | 6/2000 | Hostettler et al. |
| 6,096,070 A | 8/2000 | Ragheb et al. |
| 6,099,562 A | 8/2000 | Ding et al. |
| 6,110,188 A | 8/2000 | Narciso, Jr. |
| 6,110,483 A | 8/2000 | Whitbourne et al. |
| 6,113,629 A | 9/2000 | Ken |
| 6,120,536 A | 9/2000 | Ding et al. |
| 6,120,904 A | 9/2000 | Hostettler et al. |
| 6,121,027 A | 9/2000 | Clapper et al. |
| 6,129,761 A | 10/2000 | Hubbell |
| 6,153,252 A | 11/2000 | Hossainy et al. |
| 6,165,212 A | 12/2000 | Dereume et al. |
| 6,203,551 B1 | 3/2001 | Wu |
| 6,231,600 B1 | 5/2001 | Zhong |
| 6,240,616 B1 | 6/2001 | Yan |
| 6,245,753 B1 | 6/2001 | Byun et al. |
| 6,251,136 B1 | 6/2001 | Guruwaiya et al. |
| 6,254,632 B1 | 7/2001 | Wu et al. |
| 6,258,121 B1 | 7/2001 | Yang et al. |
| 6,270,788 B1 | 8/2001 | Koulik et al. |
| 6,273,913 B1 | 8/2001 | Wright et al. |
| 6,274,164 B1 | 8/2001 | Novich |
| 6,283,947 B1 | 9/2001 | Mirzaee |
| 6,283,949 B1 | 9/2001 | Roorda |
| 6,284,305 B1 | 9/2001 | Ding et al. |
| 6,287,628 B1 | 9/2001 | Hossainy et al. |
| 6,299,604 B1 | 10/2001 | Ragheb et al. |
| 6,306,176 B1 | 10/2001 | Whitbourne |
| 6,331,313 B1 | 12/2001 | Wong et al. |
| 6,335,029 B1 | 1/2002 | Kamath et al. |
| 6,346,110 B2 | 2/2002 | Wu |
| 6,358,556 B1 | 3/2002 | Ding et al. |
| 6,379,381 B1 | 4/2002 | Hossainy et al. |
| 6,383,215 B1 | 5/2002 | Sass |
| 6,395,326 B1 | 5/2002 | Castro et al. |
| 6,419,692 B1 | 7/2002 | Yang et al. |
| 6,451,373 B1 | 9/2002 | Hossainy et al. |
| 6,494,862 B1 | 12/2002 | Ray et al. |
| 6,497,729 B1 | 12/2002 | Moussy et al. |
| 6,503,538 B1 | 1/2003 | Chu et al. |
| 6,503,556 B2 | 1/2003 | Harish et al. |
| 6,503,954 B1 | 1/2003 | Bhat et al. |
| 6,506,437 B1 | 1/2003 | Harish et al. |
| 6,527,801 B1 | 3/2003 | Dutta |
| 6,527,863 B1 | 3/2003 | Pacetti et al. |
| 6,540,776 B2 | 4/2003 | Sanders Millare et al. |
| 6,544,223 B1 | 4/2003 | Kokish |
| 6,544,543 B1 | 4/2003 | Buchko et al. |
| 6,544,582 B1 | 4/2003 | Yoe |
| 6,555,157 B1 | 4/2003 | Hossainy |
| 6,558,733 B1 | 5/2003 | Hossainy et al. |
| 6,565,659 B1 | 5/2003 | Pacetti et al. |
| 6,572,644 B1 | 6/2003 | Moein |
| 6,585,765 B1 | 7/2003 | Hossainy et al. |
| 6,585,926 B1 | 7/2003 | Mirzaee |
| 6,605,154 B1 | 8/2003 | Villareal |
| 6,656,216 B1 | 12/2003 | Hossainy |
| 6,656,506 B1 | 12/2003 | Wu et al. |
| 6,663,662 B2 | 12/2003 | Pacetti et al. |
| 6,663,880 B1 | 12/2003 | Roorda et al. |
| 6,673,154 B1 | 1/2004 | Pacetti et al. |
| 6,703,040 B2 | 3/2004 | Katsarava |
| 6,712,845 B2 | 3/2004 | Hossainy |
| 6,743,462 B1 | 6/2004 | Pacetti |
| 6,753,071 B1 | 6/2004 | Pacetti |
| 6,758,859 B1 | 7/2004 | Dang et al. |
| 6,790,228 B2 | 9/2004 | Hossainy |
| 6,818,063 B1 | 11/2004 | Kerrigan |
| 6,824,559 B2 | 11/2004 | Michal |
| 6,926,919 B1 | 8/2005 | Hossainy et al. |
| 6,972,054 B2 | 12/2005 | Kerrigan |
| 7,005,137 B1 | 2/2006 | Hossainy et al. |
| 7,022,334 B1 | 4/2006 | Ding |
| 7,056,591 B1 | 6/2006 | Pacetti et al. |
| 7,060,093 B2 | 6/2006 | Dang |
| 7,074,276 B1 | 7/2006 | Van Sciver et al. |
| 7,115,300 B1 | 10/2006 | Hossainy et al. |
| 7,135,038 B1 | 11/2006 | Limon |
| 7,166,680 B2 | 1/2007 | Desnoyer |
| 7,169,178 B1 | 1/2007 | Santos et al. |
| 7,175,874 B1 | 2/2007 | Pacetti |
| 7,201,935 B1 | 4/2007 | Claude et al. |
| 7,202,325 B2 | 4/2007 | Hossainy |
| 7,217,426 B1 | 5/2007 | Hossainy |
| 7,232,490 B1 | 6/2007 | Hossainy |
| 7,232,573 B1 | 6/2007 | Ding |
| 7,244,443 B2 | 7/2007 | Pacetti |
| 7,247,313 B2 | 7/2007 | Roorda et al. |
| 7,255,891 B1 | 8/2007 | Pacetti |
| 7,261,946 B2 | 8/2007 | Claude |
| 7,288,609 B1 | 10/2007 | Pacetti |
| 7,294,329 B1 | 11/2007 | Ding |
| 7,311,980 B1 | 12/2007 | Hossainy et al. |
| 7,323,209 B1 | 1/2008 | Esbeck et al. |
| 7,329,413 B1 | 2/2008 | Pacetti |
| 7,335,265 B1 | 2/2008 | Hossainy |
| 7,335,391 B1 | 2/2008 | Pacetti |
| 7,341,630 B1 | 3/2008 | Pacetti |
| 2001/0007083 A1 | 7/2001 | Roorda |
| 2001/0018469 A1 | 8/2001 | Chen et al. |
| 2001/0029351 A1 | 10/2001 | Falotico et al. |
| 2001/0037145 A1 | 11/2001 | Guruwaiya et al. |
| 2002/0077693 A1 | 6/2002 | Barclay et al. |
| 2002/0091433 A1 | 7/2002 | Ding et al. |
| 2002/0155212 A1 | 10/2002 | Hossainy |
| 2003/0065377 A1 | 4/2003 | Davila et al. |
| 2003/0073961 A1 | 4/2003 | Happ |
| 2003/0099712 A1 | 5/2003 | Jayaraman |
| 2003/0104028 A1 | 6/2003 | Hossainy et al. |
| 2003/0105518 A1 | 6/2003 | Dutta |
| 2003/0158517 A1 | 8/2003 | Kokish |
| 2003/0190406 A1 | 10/2003 | Hossainy |
| 2004/0018228 A1* | 1/2004 | Fischell et al. ............... 424/450 |
| 2004/0047980 A1 | 3/2004 | Pacetti |
| 2004/0052858 A1 | 3/2004 | Wu et al. |
| 2004/0054104 A1 | 3/2004 | Pacetti |
| 2004/0060508 A1 | 4/2004 | Pacetti |
| 2004/0062853 A1 | 4/2004 | Pacetti et al. |
| 2004/0063805 A1 | 4/2004 | Pacetti et al. |
| 2004/0071861 A1 | 4/2004 | Mandrusov |
| 2004/0072922 A1 | 4/2004 | Hossainy |
| 2004/0073298 A1 | 4/2004 | Hossainy |
| 2004/0086542 A1 | 5/2004 | Hossainy |
| 2004/0096476 A1 | 5/2004 | Uhrich et al. |
| 2004/0142015 A1 | 7/2004 | Hossainy et al. |
| 2004/0162609 A1 | 8/2004 | Hossainy et al. |
| 2004/0180039 A1* | 9/2004 | Toner et al. ............... 424/93.2 |
| 2004/0180132 A1 | 9/2004 | Pacetti |
| 2004/0182312 A1 | 9/2004 | Pacetti et al. |
| 2004/0191405 A1 | 9/2004 | Kerrigan |
| 2004/0253203 A1 | 12/2004 | Hossainy |
| 2005/0021127 A1 | 1/2005 | Kawula |
| 2005/0025799 A1 | 2/2005 | Hossainy |
| 2005/0032826 A1* | 2/2005 | Mollison et al. ............... 514/291 |
| 2005/0074544 A1 | 4/2005 | Pacetti et al. |
| 2005/0112170 A1 | 5/2005 | Hossainy et al. |
| 2005/0112171 A1 | 5/2005 | Tang et al. |
| 2005/0118344 A1 | 6/2005 | Pacetti |
| 2005/0137381 A1 | 6/2005 | Pacetti |
| 2005/0147647 A1 | 7/2005 | Glauser et al. |

(56) References Cited

U.S. PATENT DOCUMENTS

| | | | |
|---|---|---|---|
| 2005/0169957 A1 | 8/2005 | Hossainy | |
| 2005/0175666 A1 | 8/2005 | Ding | |
| 2005/0208091 A1 | 9/2005 | Pacetti | |
| 2005/0208093 A1* | 9/2005 | Glauser et al. | 424/423 |
| 2005/0214339 A1 | 9/2005 | Tang et al. | |
| 2005/0226991 A1 | 10/2005 | Hossainy et al. | |
| 2005/0244363 A1 | 11/2005 | Hossainy et al. | |
| 2005/0265960 A1 | 12/2005 | Pacetti et al. | |
| 2005/0271700 A1 | 12/2005 | Desnoyer et al. | |
| 2005/0287184 A1 | 12/2005 | Hossainy et al. | |
| 2006/0002968 A1 | 1/2006 | Stewart et al. | |
| 2006/0034888 A1 | 2/2006 | Pacetti et al. | |
| 2006/0043650 A1 | 3/2006 | Hossainy et al. | |
| 2006/0062824 A1 | 3/2006 | Pacetti et al. | |
| 2006/0089485 A1 | 4/2006 | Desnoyer et al. | |
| 2006/0095122 A1 | 5/2006 | Pacetti | |
| 2006/0115449 A1 | 6/2006 | Pacetti | |
| 2006/0134165 A1 | 6/2006 | Pacetti | |
| 2006/0136048 A1 | 6/2006 | Pacetti et al. | |
| 2007/0032285 A1 | 2/2007 | Wolf | |

FOREIGN PATENT DOCUMENTS

| | | | |
|---|---|---|---|
| EP | 0 604 022 | | 6/1994 |
| EP | 0 623 354 | | 11/1994 |
| EP | 0 665 023 | | 8/1995 |
| EP | 0 701 802 | | 3/1996 |
| EP | 0 716 836 | | 6/1996 |
| EP | 0 809 999 | | 12/1997 |
| EP | 0 832 655 | | 4/1998 |
| EP | 0 850 651 | | 7/1998 |
| EP | 0 879 595 | | 11/1998 |
| EP | 0 910 584 | | 4/1999 |
| EP | 0 923 953 | | 6/1999 |
| EP | 0 947 205 | | 10/1999 |
| EP | 0 953 320 | | 11/1999 |
| EP | 0 970 711 | | 1/2000 |
| EP | 0 982 041 | | 3/2000 |
| EP | 1 273 314 | | 1/2003 |
| JP | 2001-190687 | | 7/2001 |
| SE | 2004/021976 | * | 3/2004 |
| WO | WO 91/12846 | | 9/1991 |
| WO | WO 95/10989 | | 4/1995 |
| WO | WO 96/40174 | | 12/1996 |
| WO | WO 97/10011 | | 3/1997 |
| WO | WO 97/45105 | | 12/1997 |
| WO | WO 97/46590 | | 12/1997 |
| WO | WO 98/17331 | | 4/1998 |
| WO | WO 98/36784 | | 8/1998 |
| WO | WO 99/01118 | | 1/1999 |
| WO | WO 99/38546 | | 8/1999 |
| WO | WO 99/63981 | | 12/1999 |
| WO | WO 00/02599 | | 1/2000 |
| WO | WO 00/12147 | | 3/2000 |
| WO | WO 00/18446 | | 4/2000 |
| WO | WO 00/64506 | | 11/2000 |
| WO | WO 01/01890 | | 1/2001 |
| WO | WO 01/15751 | | 3/2001 |
| WO | WO 01/17577 | | 3/2001 |
| WO | WO 01/45763 | | 6/2001 |
| WO | WO 01/49338 | | 7/2001 |
| WO | WO 01/52915 | | 7/2001 |
| WO | WO 01/74414 | | 10/2001 |
| WO | WO 01/78800 | | 10/2001 |
| WO | WO 02/03890 | | 1/2002 |
| WO | WO 02/26162 | | 4/2002 |
| WO | WO 02/34311 | | 5/2002 |
| WO | WO 02/40558 | | 5/2002 |
| WO | WO 02/056790 | | 7/2002 |
| WO | WO 02/071944 | | 9/2002 |
| WO | WO 03/000308 | | 1/2003 |
| WO | WO 03/022323 | | 3/2003 |
| WO | WO 03/022324 | | 3/2003 |
| WO | WO 03/028780 | | 4/2003 |
| WO | WO 03/037223 | | 5/2003 |
| WO | WO 03/039612 | | 5/2003 |
| WO | WO 2004/021976 | | 3/2004 |
| WO | WO 2005/000939 | | 1/2005 |

OTHER PUBLICATIONS

U.S. Appl. No. 10/705,546, filed Nov. 10, 2003, Kwok et al.
U.S. Appl. No. 10/729,728, filed Dec. 5, 2003, Pacetti.
U.S. Appl. No. 10/835,229, filed Apr. 28, 2004, Prabhu et al.
U.S. Appl. No. 10/851,411, filed May 20, 2004, Chen.
U.S. Appl. No. 10/853,924, filed May 25, 2004, Pathak.
U.S. Appl. No. 10/877,419, filed Jun. 25, 2004, Pacetti.
U.S. Appl. No. 10/883,242, filed Jun. 30, 2004, Roorda et al.
U.S. Appl. No. 10/909,795, filed Jul. 30, 2004, Ding et al.
U.S. Appl. No. 10/913,607, filed Aug. 5, 2004, Pacetti et al.
U.S. Appl. No. 10/932,364, filed Aug. 31, 2004, Foreman et al.
U.S. Appl. No. 10/976,550, filed Oct. 29, 2004, Pacetti et al.
Ruiz et al., "Phosphorylcholine-containing polyurethanes for the control of protein adsorption and cell attachment via photoimmobilized laminin oligopeptides", J. Biomater. Sci. Polym. Ed. 10(9), pp. 931-955 (1999).
European Search Rep. For appl. 05 728 269.1, mailed Jan. 19, 2009, 5 pgs.
International Search Report and Written Opinion of a PCT/US2005/008844, filed Mar. 17, 2005, mailed Sep. 13, 2005.
Anonymous, *Cardiologists Draw—Up The Dream Stent*, Clinica 710:15 (Jun. 17, 1996), http://www.dialogweb.com/cgi/document?reg=1061848202959, printer Aug. 25, 2003 (2 pages).
Anonymous, *Heparin-coated stents cut complications by 30%*, Clinica 732:17 (Nov. 18, 1996), http://www.dialogweb.com/cgi/document?reg=1061847871753, printed Aug. 25, 2003 (2 pages).
Anonymous, *Rolling Therapeutic Agent Loading Device for Therapeutic Agent Delivery or Coated Stent* (Abstract 434009), Res. Disclos. pp. 974-975 (Jun. 2000).
Anonymous, *Stenting continues to dominate cardiology*, Clinica 720:22 (Sep. 2, 1996), http://www.dialogweb.com/cgi/document?reg=1061848017752, printed Aug. 25, 2003(2 pages).
Aoyagi et al., *Preparation of cross-linked aliphatic polyester and application to thermo-responsive material*, Journal of Controlled Release 32:87-96 (1994).
Barath et al., *Low Dose of Antitumor Agents Prevents Smooth Muscle Cell Proliferation After Endothelial Injury*, JACC 13(2): 252A (Abstract) (Feb. 1989).
Barbucci et al., *Coating of commercially available materials with a new heparinizable material*, J. Biomed. Mater. Res. 25:1259-1274 (Oct. 1991).
Berrocal et al., "Improving the Blood Compatibility of Ion-Selective Electrodes by Employing Poly(MPC-co-BMA), a Copolymer Containing Phosphorylcholine, as a Membrane Coating", Am. Chem. Soc. vol. 74, No. 15, pp. 3644-3648, 2002.
Chung et al., *Inner core segment design for drug delivery control of thermo-responsive polymeric micelles*, Journal of Controlled Release 65:93-103 (2000).
Dev et al., *Kinetics of Drug Delivery to the Arterial Wall Via Polyurethane-Coated Removable Nitinol Stent: Comparative Study of Two Drugs*, Catheterization and Cardiovascular Diagnosis 34:272-278 (1995).
Dichek et al., *Seeding of Intravascular Stents with Genetically Engineered Endothelial Cells*, Circ. 80(5):1347-1353 (Nov. 1989).
Eigler et al., *Local Arterial Wall Drug Delivery from a Polymer Coated Removable Metallic Stent: Kinetics, Distribution, and Bioactivity of Forskolin*, JACC, 4A (701-1), Abstract (Feb. 1994).
Gravlee, *Heparin-Coated Cardiopulmonary Bypass Circuits*, Journal of Cardiothoracic and Vascular Anesthesia, vol. 8, No. 2, pp. 213-222 (1994).
Helmus, *Medical Device Design. A Systems Approach: Central Venous Catheteres*, 22nd International SAMPE Technical Conference, Nov. 6-8, 1990.
Helmus, *Overview of Biomedical Materials*, MRS Bulletin, pp. 33-38 (Sep. 1991).
Herdeg et al., *Antiproliferative Stent Coatings: Taxol and Related Compounds*, Semin. Intervent. Cardiol. 3:197-199 (1998).

(56) References Cited

OTHER PUBLICATIONS

Hilborn et al., "Biodegradable Phosphatidylcholine Functional Poly (E-Caprolactone)", Pol. Mat. Science and Eng. vol. 88, 2003, pp. 109-110.

Hubbell, *Pharmacologic Modification of Materials*, Cardiovascular Pathology, vol. 2, No. 3 (Suppl.), 121S-127S (1993).

Inoue et al., *An AB block copolymer of oligo(methyl methacrylate) and poly(acrylic acid) for micellar delivery of hydrophobic drugs*, Journal of Controlled Release 51:221-229 (1998).

Iwasaki, "Molecular Design and Preparation of Bioinspired Phospholipid Polymer as Novel Biomaterials", Polymer Preprints, Soc. of Polymer Science, vol. 42, No. 2, 2001, pp. 117-118.

Kataoka et al., *Block copolymer micelles as vehicles for drug delivery*, Journal of Controlled Release 24:119-132 (1993).

Levy et al., *Strategies for Treating Arterial Restenosis Using Polymeric Controlled Release Implants*, Biotechnol. Bioact. Polym. [Proc. Am. Chem. Soc. Symp.], pp. 259-268 (1994).

Li et al., "Synthesis and Hemocompatibility Evaluation of Novel Segmented Polyurethanes with Phosphatidylcholine Polar Headgroups", Chemistry of Materials 10, American Chemical Society, 1998, pp. 1596-1603.

Liu et al., *Drug release characteristics of unimolecular polymeric micelles*, Journal of Controlled Release 68:167-174 (2000).

Marconi et al., *Covalent bonding of heparin to a vinyl copolymer for biomedical applications*, Biomaterials 18(12):885-890 (1997).

Matsumaru et al., *Embolic Materials for Endovascular Treatment of Cerebral Lesions*, J. Biomater. Sci. Polymer Edn 8(7):555-569 (1997).

Miyazaki et al., *Antitumor Effect of Implanted Ethylene-Vinyl Alcohol Copolymer Matrices Containing Anticancer Agents on Ehrlich Ascites Carcinoma and P388 Leukemia in Mice*, Chem. Pharm. Bull. 33(6) 2490-2498 (1985).

Miyazawa et al., *Effects of Pemirolast and Tranilast on Intimal Thickening After Arterial Injury in the Rat*, J. Cardiovasc. Pharmacol., pp. 157-162 (1997).

Nordrehaug et al., *A novel biocompatible coating applied to coronary stents*, EPO Heart Journal 14, p. 321 (P1694), Abstr. Suppl. (1993).

Ohsawa et al., *Preventive Effects of an Antiallergic Drug, Pemirolast Potassium, on Restenosis After Percutaneous Transluminal Coronary Angioplasty*, American Heart Journal 136(6):1081-1087 (Dec. 1998).

Pechar et al., *Poly(ethylene glycol) Multiblock Copolymer as a Carrier of Anti-Cancer Drug Doxorubicin*, Bioconjucate Chemistry 11(2):131-139 (Mar./Apr. 2000).

Peng et al., *Role of polymers in improving the results of stenting in coronary arteries*, Biomaterials 17:685-694 (1996).

Shigeno, *Prevention of Cerebrovascular Spasm by Bosentan, Novel Endothelin Receptor*, Chemical Abstract 125:212307 (1996).

van Beusekom et al., *Coronary stent coatings*, Coronary Artery Disease 5(7):590-596 (Jul. 1994).

Wilensky et al., *Methods and Devices for Local Drug Delivery in Coronary and Peripheral Arteries*, Trends Cardiovasc. Med. 3(5):163-170 (1993).

Yokoyama et al., *Characterization of physical entrapment and chemical conjugation of adriamycin in polymeric micelles and their design for in vivo delivery to a solid tumor*, Journal of Controlled Release 50:79-92 (1998).

\* cited by examiner

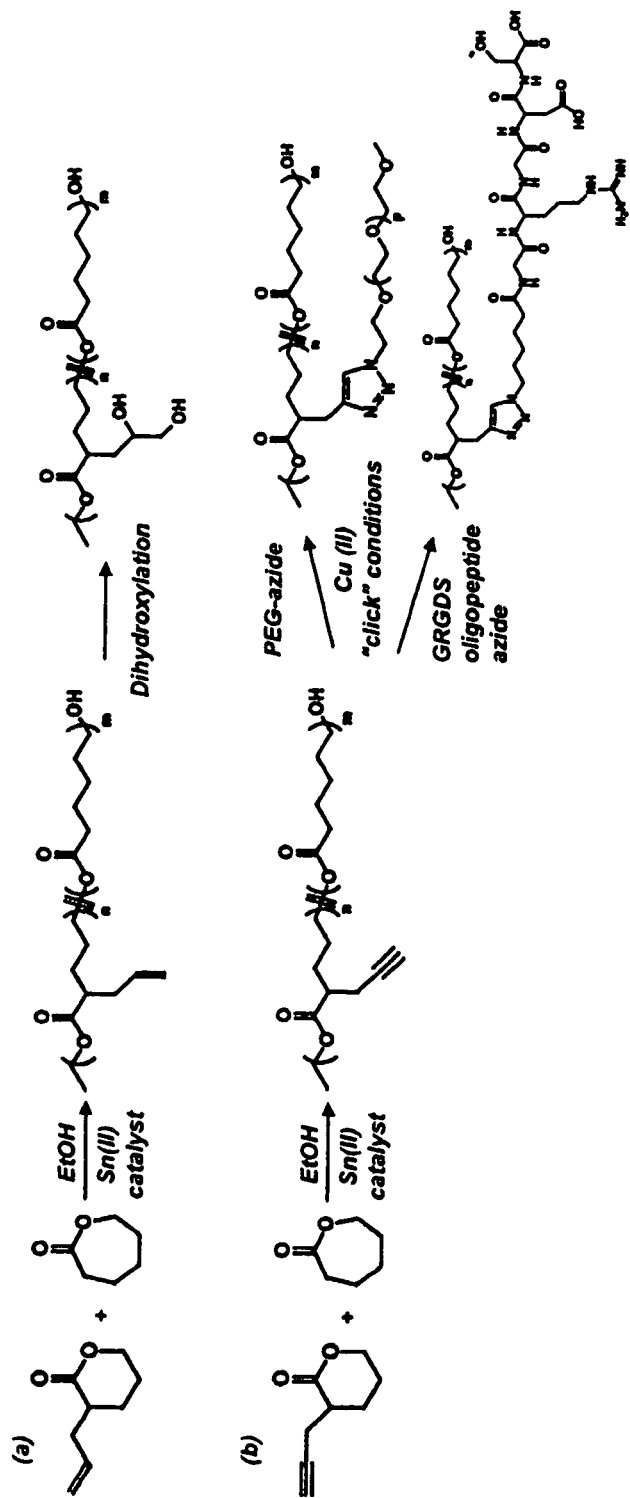

US 8,685,430 B1

TAILORED ALIPHATIC POLYESTERS FOR STENT COATINGS

CROSS-REFERENCE TO RELATED APPLICATION

This is a non-provisional application of U.S. provisional application no. 60/830,823, filed Jul. 14, 2006, the teaching of which is incorporated herein by reference in its entirety.

FIELD OF THE INVENTION

This invention generally relates to aliphatic polyester polymers for stent coatings.

DESCRIPTION OF THE BACKGROUND

Blood vessel occlusions are commonly treated by mechanically enhancing blood flow in the affected vessels, such as by employing a stent. Stents are used not only for mechanical intervention but also as vehicles for providing biological therapy. To effect a controlled delivery of an active agent in stent medication, the stent can be coated with a biocompatible polymeric coating. The biocompatible polymeric coating can function either as a permeable layer or a carrier to allow a controlled delivery of the agent.

Although stents work well mechanically, the chronic issues of restenosis and, to a lesser extent, stent thrombosis remain. Pharmacological therapy in the form of a drug delivery stent appears to be a feasible means to tackle these issues. Polymeric coatings placed onto the stent serve to act both as the drug reservoir and to control the release of the drug. One of the commercially available polymer coated products is stents manufactured by Boston Scientific. For example, U.S. Pat. Nos. 5,869,127; 6,099,563; 6,179,817; and 6,197,051, assigned to Boston Scientific Corporation, describe various compositions for coating medical devices. These compositions provide to stents described therein an enhanced biocompatibility and may optionally include a bioactive agent. U.S. Pat. No. 6,231,590 to Scimed Life Systems, Inc., describes a coating composition, which includes a bioactive agent, a collagenous material, or a collagenous coating optionally containing or coated with other bioactive agents.

There are a very large number of biodegradable polymers for coating a stent. Aliphatic polyesters represent a particularly important example, as their biocompatible and biodegradable (resorbable) properties make them attractive for a host of applications including drug delivery vehicles, tissue engineering scaffolds, implant materials, stents and stent coatings. Commercially available aliphatic polyesters such as poly(ε-caprolatone) (PCL), polylactide (PLA), and polylactide-co-glycolide (PLGA) have proven useful in many of these applications. However, these conventional polyesters do not possess functionality. The ways to functionalize these polymers outside of the backbone ester structure are limited. As a result, the application of these polymers is limited only to applications that can be satisfied by their inherent structure.

Therefore, there is a need for polymeric materials which can be tailored to meet need of a coating on a medical device.

The polymer and methods of making the polymer disclosed herein address the above described problems.

SUMMARY OF THE INVENTION

Provided herein is a phosphorylcholine (PC) functionalized aliphatic polyester (PE). The polyester can be poly(lactic acid) (PLA), poly(lactic acid-co-glycolic acid) (PLGA), poly (glycolic acid) (PGA), polycaprolactone and their copolymers (random and block). The PC tailored polyester can be used for controlling the release of an agent. The PC part of this molecule can be exposed to the surface of this coating which is desired due to its hemocompatibility while the polyester will be buried beneath to provide for release control of a drug, if present in the coating.

In some embodiments, the polymer described herein can be used to form a coating on an implantable device, which can optionally include a bioactive agent. The bioactive agent can be any diagnostic agent, therapeutic agent, or preventive agent. Some examples of such bioactive agents include, but are not limited to, paclitaxel, docetaxel, estradiol, nitric oxide donors, super oxide dismutases, super oxide dismutases mimics, 4-amino-2,2,6,6-tetramethylpiperidine-1-oxyl (4-amino-TEMPO), tacrolimus, dexamethasone, dexamethasone acetate, other dexamethasone derivatives, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin, 40-epi-(N1-tetrazolyl)-rapamycin (ABT-578), TAFA-93, biolimus-7, biolimus-9, clobetasol, momethasone derivatives, pimecrolimus, imatinib mesylate, midostaurin, prodrugs thereof, co-drugs thereof, or combinations thereof. In some embodiments, the hydrophilic bioactive agent can be a peptide (e.g., RGD, cRGD or mimetics thereof), a protein (e.g., IGF, HGF, VEGF) or a drug carrying a charge.

A medical device having a coating that includes a polymer described herein can be used to treat, prevent, or ameliorate a medical condition such as atherosclerosis, thrombosis, restenosis, hemorrhage, vascular dissection or perforation, vascular aneurysm, vulnerable plaque, chronic total occlusion, claudication, anastomotic proliferation (for vein and artificial grafts), bile duct obstruction, urethra obstruction, tumor obstruction, and combinations thereof.

BRIEF DESCRIPTION OF THE DRAWING

FIG. 1 shows the synthesis schemes for PC functionalized aliphatic polyester polymers: (a) Synthesis of 1,2-dial substituted aliphatic polyesters with tunable degradation rates and hydrophilicity; (b) synthesis of acetylene substituted aliphatic polyesters for attachment of PEG and oligopeptides by "click" cycloaddition chemistry.

DETAILED DESCRIPTION

Provided herein is a phosphorylcholine (PC) functionalize aliphatic absorbable polymers or aromatic absorbable polymers. An example of such aliphatic absorbable polymers is an aliphatic polyester. The polyester can be poly(lactic acid) (PLA), poly(lactic acid-co-glycolic acid) (PLGA), poly(glycolic acid) (PGA), polycaprolactone and their copolymers (random and block).

Some examples of aliphatic absorbable polymers include, but are not limited to, trimethylene carbonate, dioxane monomers along with LA, GA etc., poly glycerol sebacate, polyanhydrides. Some examples of aromatic absorbable polymers include, but are not limited to, polytyrosine carbonate, polyiminocarbonate, or combinations thereof.

The fictionalization of PC can be both within the backbone of the polymer or as a pendant group of the polymer backbone. For example, at least one PC moiety(ies) can be incorporated in the polymer backbone or in the pendant groups of the polymer off the polymer backbone.

The PC tailored polymers described herein can be used for controlling the release of an agent. The PC part of this molecule can be exposed to the surface of this coating which is desired due to its hemocompatibility while the polyester will be buried beneath to provide for release control of a drug, if present in the coating.

In some embodiments, the polymer described herein can be used to form a coating on an implantable device, which can optionally include a bioactive agent. The bioactive agent can be any diagnostic agent, therapeutic agent, or preventive agent. Some examples of such bioactive agents include, but are not limited to, paclitaxel, docetaxel, estradiol, nitric oxide donors, super oxide dismutases, super oxide dismutases mimics, 4-amino-2,2,6,6-tetramethylpiperidine-1-oxyl (4-amino-TEMPO), tacrolimus, dexamethasone, dexamethasone acetate, other dexamethasone derivatives, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin, 40-epi-(N1-tetrazolyl)-rapamyc in (ABT-578), TAFA-93, biolimus-7, biolimus-9, clobetasol, mometasone derivatives, pimecrolimus, imatinib mesylate, midostaurin, prodrugs thereof, co-drugs thereof, or combinations thereof. In some embodiments, the hydrophilic bioactive agent can be a peptide (e.g., RGD, cRGD or mimetics thereof), a protein (e.g., IGF, HGF, VEGF) or a drug carrying a charge.

A medical device having a coating that includes a polymer described herein can be used to treat, prevent, or ameliorate a medical condition such as atherosclerosis, thrombosis, restenosis, hemorrhage, vascular dissection or perforation, vascular aneurysm, vulnerable plaque, chronic total occlusion, claudication, anastomotic proliferation (for vein and artificial grafts), bile duct obstruction, urethra obstruction, tumor obstruction, and combinations thereof.

Phosphorylcholine Functionalization

The synthesis of aliphatic polyesters with pendent functionality, either simple organic moieties or polymeric grafts, is key to controlling these properties. FIG. 1 (route a, upper, and route b, bottom) depicts a strategy to functionalized aliphatic polyesters (PEs). As shown in FIG. 1, functionalized lactones containing either olefins (route a) or acetylenes (route b) a to the lactone carbonyl group can be prepared, then homopolymerized, or copolymerized with unfunctionalized lactones, followed by conversion of the pendent unsaturation to the desired functionality via, e.g., dihydroxylation, reaction with PEG-azide in the presence of Cu(II) or reaction with GRGDS oligopeptide azide. The post-polymerization functionalization step requires mild conditions that allow the PE to remain intact during the course of the reaction. The flexibility offered by the approach detailed meets such requirements.

In some embodiments, the PC functionalized polymers shown in FIG. 1 can be of linear, branched, hyperbranched, dendritic, or star architecture and be functionalized at the one or more chain ends. In some embodiments, these polymers can be further modified by introducing monomers that can interact with the PC groups.

As used herein, the term PC functional refers to the attribute being modified by phosphorylcholine (PC). PC modification can be readily performed by reaction of the functional groups on the polymers disclosed herein and PC so as to attach PC to the polymer as pendant groups, for example. In some embodiments, attaching PC to a polymer can be achieved by polymerization of a monomer including PC, with or without another monomer (see, e.g., Ruiz, L., et al., J Biomater Sci Polym Ed.; 10(9):931-55 (1999)).

In some embodiments, an alternative to the polymers structures of FIG. 1 are PE-methacrylate block copolymers and PE-acrylate block copolymers where the methacrylate and the acrylate blocks are PC functional and water-soluble and where the hydrophobic PE blocks make the structure insoluble. Under physiological conditions, once the PE blocks starts to degrade the polymer becomes more and more hydrophilic and eventually the PC block becomes water-soluble and can be cleared out.

In some embodiments, the polymer shown in FIG. 1 can be further modified to form a terpolymer with poly(ethylene glycol) (PEG), polyvinylpyrrolidone (PVP), or polyacrylamide (PAAm) as an intermediate block. Such a polymer can provide advantages of (1) good mechanical property by low $T_g$ of the intermediate block and water-sorption/plasticization and/or (2) biological non-fouling property added to the potentially pro-healing nature of PC-biomimetic property. As used herein, the term "PC-biomimetic" refers to the biological attributes similar to those of PC.

The fictionalization of PC can be both within the backbone of the polymer or as a pendant group of the polymer backbone.

Coating Design

The PC functionalized polymer described above can be used to coat a medical device with different coating design.

In some embodiments, the PC functionalized polymer described herein can form a layer of coating on a stent. The layer of coating can be thin, e.g., in the 2 to 3 micron range. In some embodiments, where the coating includes a bioactive agent such as everolimus, the PC functionalized polymer can be applied as a thin topcoat on a controlled release aliphatic matrix layer (e.g., a PE matrix layer) that contains the bioactive agent. This PE layer would have the same composition as the PE that is functionalized with PC so as to achieve interfacial compatibility. The PE polymer in the matrix layer and the PE polymer functionalized by PC can be same or different. The construct can include a layer of 2 to 3 micron that provides for control of the release of drug followed by a PC functionalized PE topcoat of 1 to 2 micron.

In some embodiments, alternatively, a layer of pure-drug can be sandwiched between a primer layer or a bare metal stent surface and a PC functionalized PE topcoat of 1 to 2 micron.

In some embodiments, any of the coating constructs described above can be formed on top of a bare metal stent (BMS) scaffold or an absorbable scaffold of stent.

Bioactive Agents

In some embodiments, a coating that includes a PC functionalized polymer described herein can optionally include one or more bioactive agents. These bioactive agents can be any agent which is a therapeutic, prophylactic, or diagnostic agent. These agents can have anti-proliferative or anti-inflammatory properties or can have other properties such as anti-neoplastic, antiplatelet, anti-coagulant, anti-fibrin, anti-thrombotic, antimitotic, antibiotic, antiallergic, or antioxidant properties. Moreover, these agents can be cystostatic agents, agents that promote the healing of the endothelium, or agents that promote the attachment, migration and proliferation of endothelial cells while quenching smooth muscle cell proliferation. Examples of suitable therapeutic and prophylactic agents include synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules, which bind to complementary DNA to inhibit transcription, and ribozymes. Some other examples of bioactive agents include antibodies, receptor ligands, enzymes, adhesion peptides, blood clotting factors, inhibitors or clot dissolving agents, such as streptokinase and tissue plasminogen activator, antigens for immunization, hormones and growth factors, oligonucleotides such as antisense oligonucleotides and ribozymes and retroviral vectors for use in gene therapy. Examples of anti-proliferative agents include rapamycin and its functional or structural derivatives, 40-O-(2-hydroxy)ethyl-rapamycin (everolimus), and its functional or structural derivatives, paclitaxel and its functional and structural derivatives. Examples of rapamycin derivatives include ABT-578, 40-O-(3-hydroxy)propyl-rapamycin, 40-O-[2-(2-hydroxy)ethoxy]ethyl-rapamycin, and 40-O-tetrazole-rapamycin. Examples of paclitaxel derivatives include docetaxel. Examples of antineoplastics and/or antimitotics include methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, thrombin inhibitors such as Angiomax® (Biogen, Inc., Cambridge, Mass.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), super oxide dismutases, super oxide dismutase mimetic, 4-amino-2,2,6,6-tetramethylpiperidine-1-oxyl (4-amino-TEMPO), estradiol, anticancer agents, dietary supplements such as various vitamins, and a combination thereof. Examples of anti-inflammatory agents including steroidal and non-steroidal anti-inflammatory agents include biolimus, tacrolimus, dexamethasone, dexamethasone derivatives, mometasone, mometasone derivatives, clobetasol, other corticosteroids or combinations thereof. Examples of such cytostatic substances include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.). An example of an antiallergic agent is permirolast potassium. Other therapeutic substances or agents which may be appropriate include alpha-interferon, pimecrolimus, imatinib mesylate, midostaurin, and genetically engineered epithelial cells. The foregoing substances can also be used in the form of prodrugs or co-drugs thereof. The foregoing substances also include metabolites thereof and/or prodrugs of the metabolites. The foregoing substances are listed by way of example and are not meant to be limiting. Other active agents which are currently available or that may be developed in the future are equally applicable.

In some embodiments, a coating including a polymer(s) described herein can specifically exclude any one or more of the above described agents.

The dosage or concentration of the bioactive agent required to produce a favorable therapeutic effect should be less than the level at which the bioactive agent produces toxic effects and greater than the level at which non-therapeutic results are obtained. The dosage or concentration of the bioactive agent can depend upon factors such as the particular circumstances of the patient, the nature of the trauma, the nature of the therapy desired, the time over which the ingredient administered resides at the vascular site, and if other active agents are employed, the nature and type of the substance or combination of substances. Therapeutically effective dosages can be determined empirically, for example by infusing vessels from suitable animal model systems and using immunohistochemical, fluorescent or electron microscopy methods to detect the agent and its effects, or by conducting suitable in vitro studies. Standard pharmacological test procedures to determine dosages are understood by those of ordinary skill in the art.

Examples of Medical Devices

As used herein, a medical device may be any suitable medical substrate that can be implanted in a human or veterinary patient. Examples of such medical devices include self-expandable stents, balloon-expandable stents, stent-grafts, grafts (e.g., aortic grafts), heart valve prostheses, cerebrospinal fluid shunts, pacemaker electrodes, catheters, and endocardial leads (e.g., FINELINE® and ENDOTAK®, available from Guidant Corporation, Santa Clara, Calif.), anastomotic devices and connectors, orthopedic implants such as screws, spinal implants, and electro-stimulatory devices. The underlying structure of the device can be of virtually any design. The device can be made of a metallic material or an alloy such as, but not limited to, cobalt chromium alloy (ELGILOY®), stainless steel (316L), high nitrogen stainless steel, e.g., BIODUR® 108, cobalt chrome alloy L-605, "MP35N," "MP20N," ELASTINITE® (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. Devices made from bioabsorbable (e.g., bioabsorbable stent) or biostable polymers could also be used with the embodiments of the present invention.

Method of Use

Preferably, the medical device is a stent. The stent described herein is useful for a variety of medical procedures, including, by way of example, treatment of obstructions caused by tumors in bile ducts, esophagus, trachea/bronchi and other biological passageways. A stent having the above-described coating is particularly useful for treating diseased regions of blood vessels caused by lipid deposition, monocyte or macrophage infiltration, or dysfunctional endothelium or a combination thereof, or occluded regions of blood vessels caused by abnormal or inappropriate migration and proliferation of smooth muscle cells, thrombosis, and restenosis. Stents may be placed in a wide array of blood vessels, both arteries and veins. Representative examples of sites include the iliac, renal, carotid and coronary arteries.

For implantation of a stent, an angiogram is first performed to determine the appropriate positioning for stent therapy. An angiogram is typically accomplished by injecting a radiopaque contrasting agent through a catheter inserted into an artery or vein as an x-ray is taken. A guidewire is then advanced through the lesion or proposed site of treatment. Over the guidewire is passed a delivery catheter that allows a stent in its collapsed configuration to be inserted into the passageway. The delivery catheter is inserted either percutaneously or by surgery into the femoral artery, radial artery, brachial artery, femoral vein, or brachial vein, and advanced into the appropriate blood vessel by steering the catheter through the vascular system under fluoroscopic guidance. A stent having the above-described coating may then be expanded at the desired area of treatment. A post-insertion angiogram may also be utilized to confirm appropriate positioning.

The implantable device can be implanted in any mammal, e.g., an animal or a human being. In some embodiments, the implantable device can be implanted in a patient in need of treatment by the implantable device. The treatment can be angioplasty or other type of treatments involving an implantable device.

A patient who receives the implantable device described herein can be male or female under normal body condition (e.g., normal weight) or abnormal body condition (e.g., underweight or overweight). The patient can be in any age, preferably, the patient is in an age ranging from about 40 to 70 years. An index for measuring the body condition of a patient is BMI (body mass index). A patient can have a BMI ranging from about 18 to about 30 or above.

The implantable device described herein can be used to treat or ameliorate a medical condition such as atherosclerosis, thrombosis, restenosis, hemorrhage, vascular dissection or perforation, vascular aneurysm, vulnerable plaque, chronic total occlusion, claudication, type-II diabetes, anastomotic proliferation for vein and artificial grafts, bile duct obstruction, ureter obstruction, tumor obstruction, or combinations thereof.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

We claim:

1. A coating on a medical device, comprising a polyester (PE) polymer and a phosphorylcholine (PC) functionalized aliphatic absorbable polymer,
   wherein the PE polymer is included in a matrix layer comprising a bioactive agent,
   wherein the phosphorylcholine (PC) functionalized aliphatic absorbable polymer is included in a topcoat of a thickness from about 1 to 2 microns on top of the matrix layer, and
   wherein the phosphorylcholine (PC) functionalized aliphatic absorbable polymer comprises poly glycerol sebacate.

2. The coating of claim 1 formed on a bare metal stent.

3. The coating of claim 1, wherein the bioactive agent is selected from paclitaxel, docetaxel, estradiol, 17-beta-estradiol, nitric oxide donors, super oxide dismutases, 4 amino-2,2,6,6-tetramethylpiperidine-1-oxyl (4-amino-TEMPO), tacrolimus, dexamethasone, dexamethasone acetate, rapamycin, 40-O-(2-hydroxy)ethyl-rapamycin (everolimus), 40-O-(3-hydroxy)propyl-rapamycin, 40-O-[2-(2-hydroxy)ethoxy]ethyl-rapamycin, 40-O-tetrazole-rapamycin, 40-epi-(N1-tetrazolyl)-rapamycin (ABT-578), γ-hiridun, clobetasol, mometasone, pimecrolimus, imatinib mesylate, midostaurin, and combinations of these.

4. The coating of claim 1, wherein the medical device is a bioabsorbable stent.

5. The coating of claim 1, wherein the medical device is a stent.

6. The coating of claim 4, wherein the bioactive agent is selected from paclitaxel, docetaxel, estradiol, 17-beta-estradiol, nitric oxide donors, super oxide dismutases, 4 amino-2,2,6,6-tetramethylpiperidine-1-oxyl (4-amino-TEMPO), tacrolimus, dexamethasone, dexamethasone acetate, rapamycin, 40-O-(2-hydroxy)ethyl-rapamycin (everolimus), 40-O-(3-hydroxy)propyl-rapamycin, 40-O-[2-(2-hydroxy)ethoxy]ethyl-rapamycin, 40-O-tetrazole-rapamycin, 40-epi-(N1-tetrazolyl)-rapamycin (ABT-578), γ-hiridun, clobetasol, mometasone, pimecrolimus, imatinib mesylate, midostaurin, and combinations of these.

7. The coating of claim 1, wherein the PC functionalized aliphatic absorbable polymer comprises at least one PC moiety within the backbone of the polymer or as a pendant group off the polymer backbone.

8. A method of forming PC functionalized aliphatic polyester, comprising
   polymerizing or copolymerizing lactone monomers that comprise at least one monomer comprising an olefinic or acetylenic functionality α (alpha) to the carbonyl group of the lactone group to form an aliphatic polyester polymer or copolymer comprising the olefinic or acetylenic functionality,
   functionalizing the olefinic or acetylenic functionality in the aliphatic polyester polymer or copolymer to generate a functionalized aliphatic polyester polymer or copolymer, and
   attaching PC to the functionalized aliphatic polyester polymer or copolymer to generate the PC funtionalized aliphatic polyester;
   wherein the aliphatic polyester polymer or copolymer comprises poly glycerol sebacate.

9. A method of treating or ameliorating a medical condition, comprising implanting in a patient a medical device comprising the coating according to claim 1.

10. A method of treating or ameliorating a medical condition, comprising implanting in a patient a medical device comprising the coating according to claim 6.

* * * * *

UNITED STATES PATENT AND TRADEMARK OFFICE
CERTIFICATE OF CORRECTION

PATENT NO. : 8,685,430 B1
APPLICATION NO. : 11/827783
DATED : April 1, 2014
INVENTOR(S) : Trollsas et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1317 days.

Signed and Sealed this
Ninth Day of August, 2016

Michelle K. Lee
*Director of the United States Patent and Trademark Office*